United States Patent
Ko et al.

(10) Patent No.: US 12,102,419 B2
(45) Date of Patent: Oct. 1, 2024

(54) APPARATUS AND METHOD FOR PROCESSING BIO-INFORMATION

(71) Applicant: SAMSUNG ELECTRONICS CO., LTD., Suwon-si (KR)

(72) Inventors: Byung Hoon Ko, Hwaseong-si (KR); Seung Keun Yoon, Seoul (KR); Jong Wook Lee, Suwon-si (KR); Dae Geun Jang, Yongin-si (KR); Chang Mok Choi, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1495 days.

(21) Appl. No.: 15/906,762

(22) Filed: Feb. 27, 2018

(65) Prior Publication Data
US 2019/0110698 A1    Apr. 18, 2019

(30) Foreign Application Priority Data
Oct. 13, 2017   (KR) .......................... 10-2017-0133567

(51) Int. Cl.
*A61B 5/021*     (2006.01)
*A61B 5/00*      (2006.01)
(Continued)

(52) U.S. Cl.
CPC ...... *A61B 5/02108* (2013.01); *A61B 5/02125* (2013.01); *G16H 40/63* (2018.01);
(Continued)

(58) Field of Classification Search
CPC . A61B 5/02108; A61B 5/02125; A61B 5/002; A61B 5/02416; A61B 5/053;
(Continued)

(56) References Cited

U.S. PATENT DOCUMENTS 7,722,544 B2   5/2010   Williams et al.
7,785,263 B2   8/2010   Roteliuk et al.
(Continued)

FOREIGN PATENT DOCUMENTS

EP    2 211 700       4/2009
JP    2009-213636 A   9/2009
(Continued)

OTHER PUBLICATIONS

Patzak et al., "Continuous blood pressure measurement using the pulse transit time: Comparison to intra-arterial measurement", Blood Pressure, Mar. 2015, pp. 1-5, DOI: 10.3109/08037051.2015.1030901.

(Continued)

*Primary Examiner* — Yi-Shan Yang
*Assistant Examiner* — Joseph A Tombers
(74) *Attorney, Agent, or Firm* — Sughrue Mion, PLLC

(57) ABSTRACT

A bio-information processing apparatus may include: a bio-signal measurer configured to measure a bio-signal; a bio-information receiver configured to receive first bio-information; and a processor configured to estimate second bio-information based on the bio-signal, and to correct the second bio-information based on measurement circumstances of the first bio-information and the second bio-information.

17 Claims, 7 Drawing Sheets

(51) Int. Cl.
*A61B 5/024* (2006.01)
*A61B 5/053* (2021.01)
*G16H 40/63* (2018.01)
*G16H 50/30* (2018.01)

(52) U.S. Cl.
CPC .............. *G16H 50/30* (2018.01); *A61B 5/002* (2013.01); *A61B 5/02416* (2013.01); *A61B 5/053* (2013.01); *A61B 5/7207* (2013.01); *A61B 5/7246* (2013.01); *A61B 5/7267* (2013.01); *A61B 2560/0228* (2013.01)

(58) Field of Classification Search
CPC ... A61B 5/7207; A61B 5/7246; A61B 5/7267; A61B 2560/0228; A61B 5/7235; G16H 40/63; G16H 50/30
See application file for complete search history.

(56) References Cited

U.S. PATENT DOCUMENTS

| | | | |
|---|---|---|---|
| 8,038,623 | B2 | 10/2011 | Williams et al. |
| 8,182,429 | B2 | 5/2012 | Mason |
| 8,945,016 | B2 | 2/2015 | Voss et al. |
| 2010/0312126 | A1 | 12/2010 | Williams et al. |
| 2011/0257540 | A1 | 10/2011 | Sawanoi et al. |
| 2013/0226012 | A1* | 8/2013 | Kinoshita .......... A61B 5/02108 600/490 |
| 2013/0245467 | A1 | 9/2013 | St. Pierre et al. |
| 2015/0208942 | A1* | 7/2015 | Bar-Tal .................. A61B 5/352 600/509 |
| 2016/0081563 | A1 | 3/2016 | Wiard et al. |
| 2016/0345844 | A1 | 12/2016 | McCombie et al. |
| 2017/0105637 | A1 | 4/2017 | Akl et al. |
| 2017/0112396 | A1 | 4/2017 | Pfeiffer et al. |
| 2017/0127983 | A1 | 5/2017 | Spegazzini et al. |
| 2017/0172431 | A1 | 6/2017 | Kim et al. |
| 2017/0238819 | A1* | 8/2017 | Waller ................. A61B 5/4875 |
| 2018/0085011 | A1* | 3/2018 | Ma ..................... A61B 5/02125 |
| 2018/0140210 | A1* | 5/2018 | Jelfs .................. A61B 5/02427 |

FOREIGN PATENT DOCUMENTS

| | | |
|---|---|---|
| KR | 10-2007-0056925 A | 6/2007 |
| KR | 10-2013-0095862 A | 8/2013 |
| KR | 10-2017-0073051 A | 6/2017 |
| WO | 2016/155138 A1 | 10/2016 |

OTHER PUBLICATIONS

Communication dated Nov. 23, 2022 issued by the Korean Intellectual Property Office in Korean Patent Application No. 10-2017-0133567.

* cited by examiner

APPARATUS AND METHOD FOR PROCESSING BIO-INFORMATION

CROSS-REFERENCE TO RELATED APPLICATION(S)

This application claims priority from Korean Patent Application No. 10-2017-0133567, filed on Oct. 13, 2017 in the Korean Intellectual Property Office, the disclosure of which is incorporated herein by reference in its entirety.

BACKGROUND

1. Field

Apparatuses and methods consistent with exemplary embodiments relate to processing bio-information, and more particularly to an apparatus and method for processing bio-information of a subject.

2. Description of the Related Art

A continuous monitoring system or application is being developed in which monitoring is performed in a non-invasive manner by estimating or measuring diagnosis indicators (e.g., blood pressure, blood glucose, cholesterol, etc.) based on bio-signals.

However, most existing diagnostic devices use a method of estimating bio-information based on interaction and/or a causal relationship between bio-signals and bio-information, instead of using a direct measurement method, such that research is being conducted to improve accuracy of the diagnostic devices.

In the case of using, as a diagnostic device, a blood pressure measuring apparatus which continuously estimates blood pressure based on a bio-signal for measuring blood pressure (e.g., pulse transit time (PTT) and pulse wave velocity (PWV)), it may be required to correct the estimated blood pressure based on blood pressure measured by a diagnostic device, such as a common sphygmomanometer, which has high reliability, so as to accurately estimate blood pressure.

SUMMARY

According to an aspect of an exemplary embodiment, there is provided a bio-information processing apparatus including: a bio-signal measurer configured to measure a bio-signal; a bio-information receiver configured to receive first bio-information; and a processor configured to estimate second bio-information based on the measured bio-signal, and correct the second bio-information based on measurement circumstances of the first bio-information and the second bio-information.

The processor may estimate the second bio-information by synchronizing the first bio-information with the second bio-information based on a measurement time of the bio-signal and a measurement time of the first bio-information, and by correcting an offset parameter of the second bio-information based on the first bio-information.

The processor may synchronize the first bio-information with the second bio-information by determining the measurement time of the first bio-information based on at least one of a time when the first bio-information is received, a change in the bio-signal, and input of a detection time of the first bio-information.

Further, the processor may estimate the second bio-information by correcting the offset parameter of the second bio-information by applying the measured bio-signal to a pre-generated offset parameter correction model.

In this case, the processor may determine measurement circumstances based on at least one of a type of the bio-signal, a type of the first bio-information, a type of the second bio-information, a measurement point of the bio-signal, information on whether time information is included, a detection state of the bio-signal, a correction history of the second bio-information, a sampling rate, and motion noise in measuring the bio-signal.

Based on the determined measurement circumstances, the processor may determine whether to correct the second bio-information, whether to index the measurement circumstances, and whether to display and store the second bio-information.

In response to the measurement point of the bio-signal being different from a measurement point of the first bio-information, the processor may convert the bio-signal based on a bio-signal conversion model which is pre-generated based on a correlation between sample bio-signals, and estimate the second bio-information based on the converted bio-signal.

The processor may determine the measurement point based on a user's input of the and position information detected by a position detection sensor.

Further, the processor may continuously estimate the second bio-information based on a result of correcting the second bio-information based on the measurement circumstances of the first bio-information and the second bio-information.

The bio-information processing apparatus may further include an output interface configured to output at least one of the measured bio-signal, the first bio-information, the second bio-information, a result of correcting the second bio-information, information of the measurement circumstances, correction reliability of the second bio-information, warning information, a continuous measurement result, and a trend graph.

The output interface may display the measured bio-signal in a first area of a user interface, and display the corrected second bio-information in a second area of the user interface.

In response to the second bio-information being corrected at a plurality of times, the processor may update the second bio-information based on a correction result at any one time among the plurality of times.

The output interface may display an estimation result of the second bio-information that is obtained from continuously measured bio-signals in a predetermined range, and output a trend graph indicating a pattern of change of the second bio-information that is obtained from the continuously measured bio-signal.

According to an aspect of another exemplary embodiment, there is provided a bio-information processing apparatus including: a bio-signal measurer configured to measure a first bio-signal and a second bio-signal; a time recorder configured to record a first measurement time of the first bio-signal and a second measurement time of the second bio-signal; and a processor configured to estimate first bio-information and second bio-information based on the first bio-signal and the second bio-signal, and correct the second bio-information based on measurement circumstances of the first bio-information and the second bio-information.

The processor may estimate the second bio-information by synchronizing the first bio-information with the second bio-information based on the first measurement time and the second measurement time, and by correcting an offset parameter of the second bio-information based on the first bio-information.

The processor may determine the measurement circumstances based on at least one of types of the first bio-signal and the second bio-signal, type of the first bio-information and the second bio-information, measurement points of the first bio-signal and the second bio-signal, detection states of the first bio-signal and the second bio-signal, a correction history of the second bio-information, a sampling rate, and motion noise in measuring the first bio-signal and the second bio-signal.

The bio-signal measurer may include a first measurer disposed at a first surface of the bio-information processing apparatus, and a second measurer disposed at a second surface of the bio-information processing apparatus.

According to an aspect of another exemplary embodiment, there is provided a bio-information processing method, including: measuring a bio-signal; receiving first bio-information; estimating second bio-information based on the measured bio-signal; and correcting the second bio-information based on measurement circumstances of the first bio-information and the second bio-information.

In this case, the estimating of the second bio-information may include: synchronizing the first bio-information with the second bio-information based on a measurement time of the bio-signal and a measurement time of the first bio-information; and correcting an offset parameter of the second bio-information based on the first bio-information.

Further, the estimating the second bio-information may include synchronizing the first bio-information with the second bio-information by determining the measurement time of the first bio-information based on at least one of a time when the first bio-information is received, a change in the bio-signal, and input of a detection time of the first bio-information.

The correcting the second bio-information may include determining the measurement circumstances based on a type of the bio-signal, a type of the first bio-information, a measurement point of the bio-signal, information on whether time information is included, a detection state of the bio-signal, a correction history of the second bio-information, a sampling rate, and motion noise in measuring the bio-signal.

Further, the correcting of the second bio-information may include determining, based on the measurement circumstances, whether to correct the second bio-information, whether to index the measurement circumstances, and whether to display and store the second bio-information.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
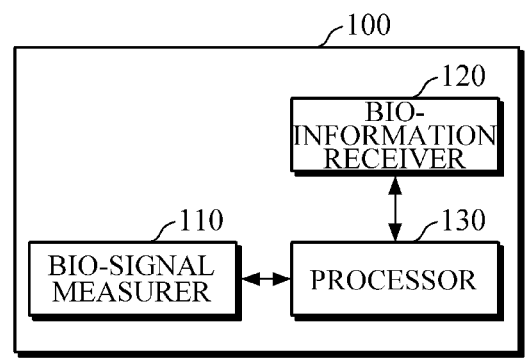
FIG. 1 is a block diagram illustrating a bio-information processing apparatus according to an exemplary embodiment.

Exemplary embodiments are described in greater detail below with reference to the accompanying drawings.

In the following description, like drawing reference numerals are used for like elements, even in different drawings. The relative size and depiction of these elements may be exaggerated for clarity, illustration, and convenience.

The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating a bio-information processing apparatus according to an exemplary embodiment. The bio-information processing apparatus 100 may estimate bio-information based on a measured bio-signal, and may correct the estimated bio-information based on reference bio-information, thus accurately estimating bio-information based on the measured bio-signal.

For example, the bio-information processing apparatus 100 may estimate bio-information which has correlation with a bio-signal measured at a specific body portion of a user (e.g., upper arm, finger, wrist, etc.). Here, the bio-signal may include a pulse, pulse waves, a skin spectrum, and the like, but is not limited thereto, and may include various bio-signals measured by a non-invasive method. Further, the bio-information estimated from the bio-signal is bio-information that has some correlation with the measured bio-signal, and may include blood pressure, blood glucose, cholesterol, and the like, but is not limited thereto, and may include various in vivo components.

Hereinafter, for convenience of explanation, the bio-information processing apparatus 100 will be described based on an exemplary embodiment in which blood pressure is estimated from a pulse or a pulse wave signal, and the estimated blood pressure is corrected, but the bio-information processing apparatus 100 is not limited thereto.

In the exemplary embodiment, the bio-information processing apparatus 100 may perform correction by synchronizing the estimated bio-information with reference bio-information.

An offset parameter, which is applied to estimation of the bio-information, may vary depending on a measurement point (e.g., wrist, finger, etc.) of a bio-signal, the types of estimated bio-information (e.g., blood pressure, heart rate, blood glucose, etc.), or individual physical characteristics (e.g. age, gender, weight, height, etc.). In this case, the bio-information processing apparatus 100 may estimate bio-information more accurately by temporally synchronizing the estimated bio-information with reference bio-information and by adjusting the offset parameter of the estimated bio-information based on the reference bio-information. For example, the following Equation 1 may be an exemplary estimation model for estimating a blood pressure value from a pulse wave signal.

$$\text{Blood pressure}_{estimated}(t) = f(a,b) + c \qquad \text{[Equation 1]}$$

Herein, function $f(a,b)$ may be an estimation model for estimating a blood pressure value from features values a and b of the pulse wave signal which is measured continuously according to time t, and may be a regression model generated based on a correlation between the pulse wave signal and blood pressure, or a learning model which is pre-generated to estimate bio-information by machine learning based on the feature values a and b. Further, c is an offset parameter, and may be represented by a constant value according to the types and measurement points of bio-information to be estimated.

In the case of estimating blood pressure from the pulse wave signal by using such estimation model, a value of blood pressure$_{reference}(t_1)$–blood pressure$_{estimated}(t_1)$, which is a value of difference between blood pressure$_{estimated}(t_1)$ estimated at time $t_1$ and blood pressure$_{reference}(t_1)$ measured at time $t_1$ by using a common sphygmomanometer, may be an offset parameter correction value of the blood pressure$_{estimated}(t_1)$. For example, by adding the value of difference, blood pressure$_{reference}(t_1)$–blood pressure$_{estimated}(t_1)$, to an offset parameter $c_{t1}$ which is applied to the blood pressure$_{estimated}(t_1)$ estimated at time $t_1$, the bio-information processing apparatus 100 may correct the offset parameter of the estimated Blood pressure$_{estimated}(t)$. In order to correct the offset parameter, it may be required to synchronize a measurement time of the pulse wave signal with a measurement time of the blood pressure by using the common sphygmomanometer, or measurement time information. If the two signals are not synchronized, the bio-information processing apparatus 100 may estimate a measurement time of the blood pressure measured by using the common sphygmomanometer, and may temporally synchronize the estimated measurement time of the blood pressure with the estimated bio-information.

In this manner, the bio-information processing apparatus 100 may estimate bio-information more accurately by synchronizing a measurement time of the reference bio-information with the bio-information estimated from the bio-signal, and by correcting an offset parameter of the estimated bio-information.

The bio-information processing apparatus 100 may be implemented as a software module or manufactured in the form of a hardware chip to be embedded in various types of electronic apparatuses. Examples of the electronic apparatuses may include a cellular phone, a smartphone, a tablet PC, a laptop computer, a personal digital assistant (PDA), a portable multimedia player (PMP), a navigation, an MP3 player, a digital camera, a wearable device, and the like. However, the electronic apparatus is not limited to the above examples.

Referring to FIG. 1, the bio-information processing apparatus 100 includes a bio-signal measurer 110, a bio-information receiver 120, and a processor 130. Here, the bio-information receiver 120 may include a communication module to receive bio-information from an external device which measures and stores bio-information. Further, the processor 130 may include one or more processors, a memory, and a combination thereof.

The bio-signal measurer 110 may measure a bio-signal of a user. For example, the bio-signal measurer 110 may include a contact pressure sensor or a pulse wave sensor to measure a bio-signal, and may measure a bio-signal, such as a user's pulse or pulse waves, by measuring a strain gauge using the contact pressure sensor, or by detecting an optical signal using a detector of the pulse wave sensor. The bio-signal measure 110 may include any one or any combination of a spectrometer, a body impedance analyzer, and a blood pressure monitor. For example, the spectrometer may emit a light to a user, and detect the light that is scattered or reflected from the user to determine a blood sugar level, a blood pressure, a body impedance, or a heart rate based on the detected light. The body impedance analyzer may include input contact sensors and output contact sensors. While a user is in contact with the input contact sensors and the output contact sensors, current is applied to the input contact sensors and voltage is detected from the output contact sensors. The body impedance analyzer may determine a body impedance of the user based on a value of the inputted current and a value of the detected voltage.

The bio-information receiver 120 may receive bio-information.

In the exemplary embodiment, the bio-information receiver 120 may receive first bio-information. Here, the first bio-information may be reference bio-information to be used as a reference for comparison with bio-information estimated from a bio-signal.

For example, the bio-information receiver 120 may receive the first bio-information of a user from an external device by communicating with the external device. For example, the bio-information receiver 120 may receive bio-information data of a user from an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, and the like. The bio-information receiver 120 may be also referred to a communication interface.

However, this is merely exemplary and the communication is not limited thereto. For example, the bio-information receiver 120 may receive bio-information by directly connecting to or communicating with the external device, and may also receive the bio-information via one or more relay servers for relaying communication between the bio-information receiver 120 with the external device.

Here, examples of the external device may include a cuff-type blood pressure measuring device, a medical diagnostic device, a cellular phone, a smartphone, a tablet PC, a laptop computer, a personal digital assistant (PDA), a portable multimedia player (PMP), a navigation, an MP3 player, a digital camera, a wearable device, and the like. However, the electronic device is not limited to the above examples, and may be various devices that may measure or store bio-information of a user.

The processor 130 may estimate second bi-information based on the measured bio-signal, and may correct the second bio-information based on the first bio-information.

In the exemplary embodiment, the processor 130 may estimate the second bio-information based on the bio-signal measured by the bio-signal measurer 110. For example, by using a bio-signal information estimation model (e.g., regression model, machine learning model, etc.), which defines a correlation between the measured bio-signal and bio-information, the processor 130 may estimate bio-information from the bio-signal.

For example, the processor 130 may estimate blood pressure by calculating a pulse transit time (PTT) and a pulse wave velocity (PWV) based on a pulse and/or a pulse wave signal measured by the bio-signal measurer 110, or may estimate blood pressure by using pulse wave analysis (PWA) which analyzes the shape of pulse waves.

Upon estimating the second bio-information, the processor 130 may correct the second bio-information based on the first bio-information.

In the exemplary embodiment, the processor 130 may synchronize the first bio-information with the second bio-information based on measurement time information, and may correct an offset parameter of the second bio-information based on the first bio-information. Here, the measurement time information may be time information including measurement time information of the first bio-information and/or measurement time information of the second bio-signal. For example, in the case of estimating blood pressure by calculating the pulse transit time (PTT) and the pulse wave velocity (PWV), the offset parameter may vary depending on a measurement point of a pulse or a pulse wave signal, and physical characteristics of the user, and the processor 130 may correct the offset parameter of the second bio-information based on the first bio-information, to estimate bio-information correctly.

For example, once the bio-information receiver 120 receives the first bio-information, which may be used as reference for correcting the second bio-information, from an external device (e.g., common sphygmomanometer), the processor 130 may synchronize the first bio-information with the second bio-information based on the measurement time information of the first bio-information and the second bio-information, and may correct the offset parameter of the second bio-information by calculating a difference between the first bio-information and the second bio-information.

For example, the processor 130 may determine a measurement time of the first bio-information based on a time when the first bio-information is received. For example, in the case where the bio-information receiver 120 may communicate with an external device directly or via a relay server, the processor 130 automatically recognizes a time of receiving a measurement result of bio-information from the external device, and may determine the time to be a time of starting to measure the first bio-information.

In another example, the processor 130 may determine the measurement time of the first bio-information based on a change in the measured bio-signal. For example, upon measuring the first bio-information on the upper arm by using a common sphygmomanometer (e.g., mercury sphygmomanometer, aneroid sphygmomanometer, etc.), such as a cuff-type blood pressure measuring device, the bio-signal measurer 110 may measure, as a bio-signal, pulse waves at a portion of the top of the wrist of the arm where capillary or venous blood passes and where the first bio-information of a user is measured, and/or at a portion of the bottom of the wrist where the radial artery passes. In this case, the processor 130 may measure the measurement time of the first bio-information by detecting a change in the pulse wave signal, which is detected at the top portion of the wrist where capillary or venous blood passes, and is measured by the bio-signal measurer 110 according to a degree of pressure which is applied to an upper arm artery by the common sphygmomanometer.

In another example, the processor 130 may determine the measurement time of the first bio-information based on input of a detection time of the first bio-information. The bio-information processing apparatus 100 may further include an input module to input a measurement time of the first bio-information, and the processor 130 may determine the measurement time of the first bio-information based on input of a measurement time from a user.

Further, determination of the measurement time of the first bio-information is not limited thereto, and in the case where the first bio-information, measured by an external device, includes measurement time information, the processor 130 may determine the measurement time of the first bio-information based on the included measurement time information. In this manner, even when the measurement time of the first bio-information is different from the measurement time of the second bio-information, the processor 130 may determine the measurement time of the first bio-information, and may correct the offset parameter of the second bio-information by temporally synchronizing the first bio-information with the second bio-information.

In another example, in the case where the processor 130 may not know or determine the measurement time of the first bio-information, for example, in the case where the processor 130 does not receive the first bio-information according to a user's selection or need, or in the case where the processor 130 may not receive bio-information from the bio-information receiver 120, or there are no feature points to specify a measurement time in the received first bio-information, the processor 130 may correct the offset parameter of the second bio-information by applying the measured bio-signal to a pre-generated offset parameter correction model.

Here, the offset parameter correction model may be a correction model pre-generated into one or more groups according to measurement circumstances, which include at least one of the types of a bio-signal and/or bio-information, a measurement point, a detection state of a bio-signal, a correction history of the second bio-information, a sampling rate, and motion noise in the detected bio-signal, and according to user information which includes at least one of age, gender, race, weight, body mass index (BMI), health information history of a user. For example, the offset parameter correction model may be pre-generated by a user's input and/or by machine learning, and the processor 130 may determine whether it is required to correct the offset parameter of the second bio-information, a time when the correction is required, and a correction value, by applying the second bio-information to the offset parameter correction model. In this case, determination on whether it is required to correct the second bio-information may be made based on the correction history of the second bio-information; determination on the time when the correction is required may be made by determining, based on the measurement circumstances, whether measurement circumstances are similar to previous measurement circumstances when correction was performed; and the correction value may be made based on at least one of an average value, a mean value, a highest value, and a lowest value, of offset correction values of the offset parameter correction models classified into one or more groups.

In the exemplary embodiment, the processor 130 may determine the measurement circumstances based on at least one of the types of a bio-signal and bio-information, a measurement point, a detection state of a bio-signal, a correction history of the second bio-information, a sampling rate, and motion noise in the detected bio-signal.

For example, in the case where the measurement point is an upper arm and a wrist, or a finger and a wrist, the processor 130 may determine measurement circumstances to be a case where measurement points are different. In this case, the processor 130 may obtain measurement points from a user's input of measurement points, position information detected by a position detection sensor included in the bio-information processing apparatus 100 and/or measurement point information included in bio-information received from an external device.

Further, the processor 130 may determine measurement circumstances to be a case where a bloodstream change occurs due to pressure, such as a case where a bio-signal is detected after it has not been detected, according to a detection state of a bio-signal.

For example, in the case where the measurement circumstances are determined to be a case where the measurement point of the bio-signal is not the same as the measurement point of the first bio-information, the processor 130 may convert the bio-signal based on a bio-signal conversion model which is pre-generated based on a correlation between bio-signals. For example, in the case where the measurement point of the bio-signal is a wrist, and the measurement point of the first bio-information is an upper arm or a finger, it may not be appropriate for the processor 130 to estimate the second bio-information based on a bio-signal measured at the wrist, and to correct the offset parameter of the second bio-information by comparing the first bio-information with the second bio-information.

In this case, based on a bio-signal conversion model pre-generated by measuring a bio-signal on the upper arm or the finger, and the wrist, the processor 130 may convert a bio-signal measured on the wrist into a bio-signal measured on the upper arm or the finger, and may estimate the second bio-signal based on the converted bio-signal. In this manner, even when bio-signals and/or bio-information are measured at difference measurement points, the processor 130 may estimate the second bio-information by converting a bio-signal into a bio-signal and/or bio-information measured at any point by using the bio-signal conversion model pre-generated based on a correlation between bio-signals measured at various points, such that the processor 130 may estimate and correct the second bio-information more accurately.

Upon determining the measurement circumstances, the processor 130 may determine whether to correct the second bio-information, whether to index the measurement circumstances, and whether to display and store the second bio-information. For example, if the measurement circumstances are determined to be a case where motion noise (e.g., a signal to ratio (SNR), etc.) in the detected bio-signal exceeds a predetermined threshold, the processor 130 may determine to correct the second bio-information, to index the measurement circumstances at the time of correction to the corrected second bio-signal, or to output or store the second bio-information as a result.

For example, in the case where based on the correction history of the second bio-information, the measurement circumstances are determined to be a case where correction of the second bio-information was performed within 30 minutes, the processor 130 may determine that additional correction of the second bio-information is not required. Further, the processor 130 may extract an offset parameter correction value from the correction history of the second bio-information; and in the case where the extracted offset parameter correction value is greater or less than a predetermined threshold value, the processor 130 determines that it is required to correct the second bio-information, and may estimate the second bio-information by correcting the offset parameter of the second bio-information. Here, the threshold value may be determined based on a measurement position of a bio-signal and the types of bio-information.

In this manner, by selectively varying data processing, such as correction of the second bio-information or storage of data, based on the measurement circumstances, the processor 130 may optimally use a limited operating environment.

Further, based on a correction result of the second bio-information, the processor 130 may continuously estimate the second bio-information. For example, based on the bio-signal which is continuously measured by the bio-signal measurer 110, the processor 130 may correct the offset parameter of the second bio-information, and may continuously estimate the second bio-information based on the correction result. In addition, the processor 130 may successively estimate the second bio-information by updating the offset parameter more than once if necessary.

Figure 2:
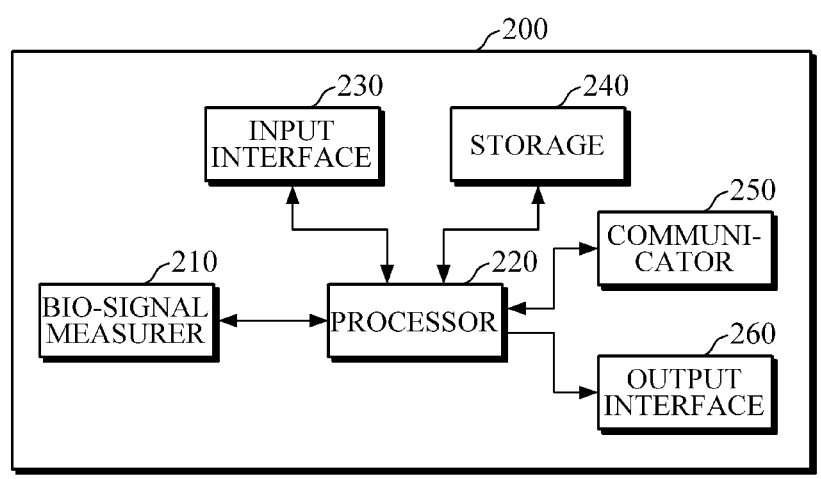
FIG. 2 is a block diagram illustrating a bio-information processing apparatus according to another exemplary embodiment.

FIG. 2 is a block diagram illustrating a bio-information processing apparatus according to another exemplary embodiment.

Referring to FIG. 2, the bio-information processing apparatus 200 includes a bio-signal measurer 210, a processor 220, an input interface 230, a storage (e.g., a memory) 240, a communicator (e.g., a communication interface or transceiver) 250, and an output interface 260. Here, the bio-signal measurer 210 and the processor 220 may perform substantially the same operations as the bio-signal measurer 110 and the processor 120 described above with reference to FIG. 1, such that description below will be made based on details that do not overlap.

The input interface 230 may receive input of various operation signals and data required for processing bio-information from a user. In the exemplary embodiment, the input interface 230 may include a keypad, a dome switch, a touch pad (static pressure/capacitance), a jog wheel, a jog switch, a hardware (H/W) button, and/or the like. Particularly, the touch pad, which forms a layer structure with a display, may be called a touch screen.

For example, the input interface 230 may receive input of at least one or more of measurement circumstances, which include at least one of the types of a bio-signal and/or bio-information, a measurement point, a detection state of a bio-signal, a correction history of the second bio-information, and a sampling rate, and user information which includes at least one of age, gender, race, weight, BMI, health information history of a user.

For example, based on the information (e.g., user information, etc.) input through the input interface 230, the processor 220 may select a correction model or a conversion model, which is appropriate for estimating bio-information of a user, from among offset parameter correction models and/or a bio-signal conversion models which are generated by being classified into one or more groups.

The storage 240 may store programs or commands for operation of the bio-information processing apparatus 200, and may store data input to and output from the bio-information processing apparatus 200. For example, the storage part 240 may store user information input through the input interface 230, bio-signal data obtained by the bio-signal measurer 210, the offset parameter correction model and/or the bio-signal conversion model, and the like.

In the exemplary embodiment, the storage 240 may store data in one or more divided storage areas.

For example, the storage 240 may divide the storage areas into a time area, a correction area, a measurement circumstance area, and a data area, and may reconstruct data stored in each of the storage areas to multi-dimensional data higher than one-dimension, to use the reconstructed data for analysis and arrangement of data. For example, each area may be a physically divided storage module, and data may be stored in a virtual divided area by labeling data. For example, the time area may store data by temporally synchronizing the measured data based on time information received from a time recording device (e.g., internal timer, etc.) of the bio-information processing apparatus 200 or an external device. The correction area may be an area for storing a bio-information estimation result or continuously estimated bio-information. The measurement circumstance area may be an area for storing information associated with measurement circumstances and reference information to classify the bio-signal data, the offset parameter correction model and/or the bio-signal conversion model, and the like into one or more groups.

The storage 240 may store data by reconstructing data, stored in each storage area, to multi-dimensional data higher than one dimension. For example, the storage 240 may synchronize data, divided into one or more groups according to the measurement circumstances, by arranging the data according to time based on time information stored in the time area, and may reconstruct the stored data by defining the one or more divided storage areas in a single dimension.

The storage 240 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the bio-information processing apparatus 200 may operate an external storage medium, such as web storage and the like, which performs a storage function of the storage 240 on the Internet.

The communicator 250 may perform communication with an external device.

In the exemplary embodiment, the communicator 250 may receive bio-information from an external device. Here, the bio-information may be reference bio-information for correcting estimated bio-information based on a bio-signal measured by the bio-signal measurer 210. Further, the communicator 250 is not limited thereto, and may receive a bio-signal from an external device, and the processor 220 may estimate the bio-information based on the received bio-signal. In this case, bio-information received from an external device or bio-information estimated based on a bio-signal received from an external device may be referred to as the first bio-information; and bio-information estimated based on the bio-signal measured by the bio-signal measurer 210 may be referred to as the second bio-information.

The communicator 250 may transmit, to the external device, user information input by a user and/or measurement circumstance information, the bio-signal measured by the bio-signal measurer 210, a bio-information processing result of the processor 220, and the like; or may receive, from the external device, various data such as the user information and/or the measurement circumstance information, the offset parameter correction model and the bio-signal conversion model, and the like.

In this case, the external device may be a database (DB) which stores the offset parameter correction model and the bio-signal conversion model, and/or a medical device which uses the bio-information processing result, a printer to print out results, or a display device which displays a disease prediction result. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 250 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, ultra-wideband (UWB) communication, Ant+ communication, WIFI communication, Radio Frequency Identification (RFID) communication, 3G communication, 4G communication, 5G communication, and the like. However, this is merely exemplary and the communication is not limited thereto.

Figure 3A:
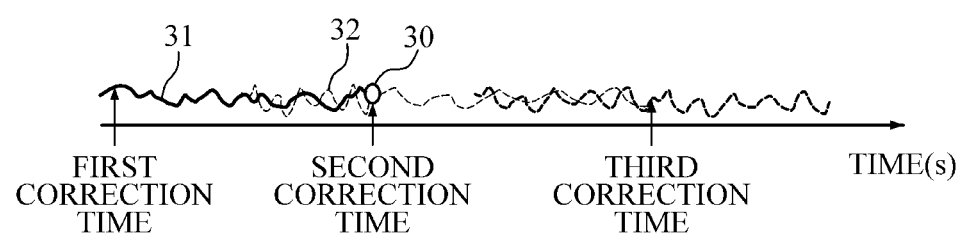
FIGS. 3A and 3B are diagrams explaining an example of outputting a bio-information processing result of a bio-information processing apparatus 200 according to an exemplary embodiment.
Figure 3B:
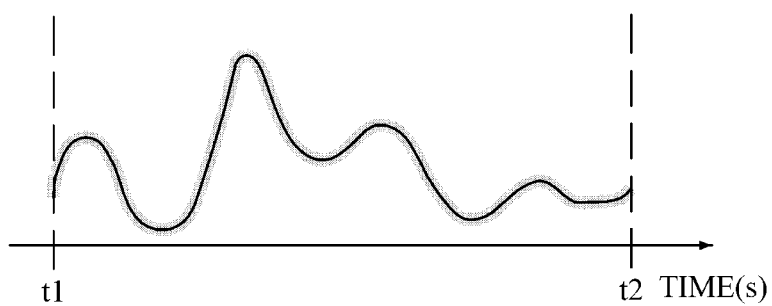

FIGS. 3A and 3B are diagrams explaining an example of outputting a bio-information processing result of the bio-information processing apparatus 200 according to an exemplary embodiment.

The output interface 260 may output, by control of the processor 220, at least one of the measured bio-signal, the first bio-information, the second bio-information, a correction result of the second bio-information, the measurement circumstance information, correction reliability of bio-information, warning information, a continuous measurement result, and a trend graph, by using at least one of an acoustic method, a visual method, and a tactile method.

To this end, the output interface 260 may include a display, a speaker, a vibrator, and/or the like.

In the exemplary embodiment, the output interface 260 may divide a display area into one or more areas, and may output different data in each area.

For example, the output interface 260 may display a user interface in the display area, and may display the measured bio-signal in a first area of the user interface, and the corrected second bio-information in a second area thereof.

For example, referring to FIG. 3A, in the case where correction of the second bio-information is performed at a plurality of times (e.g., first, second, and third correction times), the output interface 260 may output a graph 32 of the second bio-information which is updated based on a correction result at any one time among the plurality of times. For example, in the case where a user selects a correction result at any one time among the plurality of correction times, the processor 220 may update the second bio-information by correcting again existing second bio-information based the selected correction result, and the output interface 260 may output the graph 32 of the updated second bio-information as a continuous graph according to elapsed time. In this case, the output interface 260 may output the selected correction time by using an identification mark 30 of a predetermined shape, and may output a graph 31 showing the second bio-information prior to the selected correction time as a graph which is superimposed on the graph of the updated second bio-information. In this manner, based on a correction result at a specific correction time, the bio-information processing apparatus 200 may update and display values both before and after the specific correction time, thereby minimizing reduction in estimation accuracy of bio-information over elapsed time after the correction is performed.

In another example, the output interface 260 may display an estimation result of the second bio-information in a specific range for continuously measured bio-signals, and may output a trend graph of the continuous second bio-information. The trend graph may indicate a pattern of change of the continuous second bio-information.

For example, referring to FIG. 3B, the output interface 260 may display bio-information which is continuously estimated at every predetermined time interval (e.g., $t_2-t_1$) and is superimposed on one another, and may display bio-information values at each time in a range to include all the superimposed areas, such that the output interface 260 may output a trend graph which allows to determine tendency of the estimated bio-information.

Figure 4:
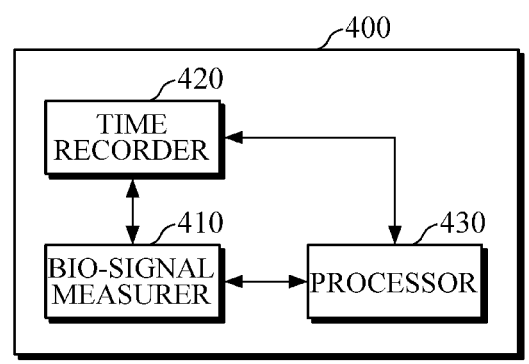
FIG. 4 is a block diagram illustrating a bio-information processing apparatus according to another exemplary embodiment.

FIG. 4 is a block diagram illustrating a bio-information processing apparatus according to another exemplary embodiment. Referring to FIG. 4, the bio-information processing apparatus 400 includes a bio-signal measurer 410, a time recorder 420, and a processor 430. Here, the processor 430 may perform substantially the same operation as the processors 130 and 220 output interface described above with reference to FIGS. 1 and 2, such that description below will be made based on details that do not overlap.

The bio-signal measurer 410 may measure a first bio-signal and a second bio-signal. For example, the bio-signal measurer 410 may include a contact pressure sensor or a pulse wave sensor required for measuring a bio-signal, and may measure a bio-signal, such as a user's pulse or pulse waves, by measuring a strain gauge using the contact pressure sensor, or by detecting an optical signal using a detector of the pulse wave sensor.

In the exemplary embodiment, the bio-signal measurer 410 may include one or more measurement modules to measure a bio-signal. In the case where the bio-signal measurer 410 includes at least two or more measurement modules, each measurement module may be disposed at different positions. In this case, at least one measurement module may be disposed at a measurement point to measure a reference bio-signal required for correction of bio-information. For example, the bio-signal measurer 410 may include a first measurer, disposed at a first surface of the bio-information processing apparatus 400, and a second measurer disposed at a second surface thereof.

For example, the bio-signal measurer 410 may measure a first bio-signal at a first measurement point (e.g., upper arm, finger, etc.), and a second bio-signal at a second measurement point (e.g., wrist, etc.). In this case, different bio-signal measurement modules are disposed separately at the first measurement point and the second measurement point, such that the first bio-signal and the second bio-signal may be measured at the same time.

In another example, as a user sequentially moves the bio-signal measurement modules of the bio-signal measurer 410 to points desired to measure a bio-signal, the bio-signal measurer 410 may measure the first bio-signal and the second bio-signal. In this case, however, temporal separation may occur between the first bio-signal and the second bio-signal, but the first bio-signal and the second bio-signal may be synchronized with each other based on time information recorded by the time recorder 420, which will be described below.

The time recorder 420 may record a measurement time of a bio-signal. For example, the time recorder 420 may record a measurement time and a continuous measurement time of the first bio-signal and the second bio-signal, and may label the measured bio-signal with time information.

For example, the bio-information processing apparatus 400 may further include a movement sensor (e.g., acceleration sensor, gyro sensor, gravity sensor, etc.), and the time recorder 420 may record the measurement time of the bio-signal and a time of sensing movement together or separately. For example, in the case where a user moves the bio-signal processing apparatus 400 to a point desired to measure a bio-signal, the time recorder 420 records a time when movement of the bio-signal processing apparatus 400 is sensed, so that the processor 430 may differentiate between bio-signals before and after the movement.

For example, in the case where measurement points or measurement times of the first bio-signal and the second bio-signal are different, or in the case where a time difference occurs due to an operation speed difference in a process of estimating bio-information based on the first bio-signal and the second bio-signal, the processor 430 may temporally synchronize the first bio-signal with the second bio-signal based on the measurement times of the bio-signals which are recorded by the time recorder 420.

The processor 430 may estimate the first bio-information and the second bio-information based on the first bio-signal measured at the first measurement point and the second bio-signal measured at the second measurement point, and may correct the second bio-information based on the measurement circumstance information of the first bio-information and the second bio-information.

Here, the second bio-information may be bio-information to be measured by the bio-information processing apparatus 400, and the first bio-information may be reference bio-information for correcting the second bio-information. To this end, the second measurement point, at which the second bio-signal is measured, may be a reference point to generate reference data, and the first measurement point and the second measurement point may generally be different positions, but may also be the same measurement point if necessary.

In the exemplary embodiment, the processor 430 may estimate blood pressure by calculating a pulse transit time (PTT) and a pulse wave velocity (PWV) based on a pulse and/or a pulse wave signal measured by the bio-signal measurer 410, or may estimate blood pressure by using pulse wave analysis (PWA) which analyzes the shape of pulse waves. However, the processor 430 is not limited thereto, and may estimate the first bio-information and the second bio-information from the first bio-signal and the second bio-signal by using a bio-information estimation model (e.g., regression model, neural network model, etc.) which defines a correlation between the measured bio-signal and the bio-information.

Upon estimating the first bio-information and the second bio-information, the processor 430 may correct the second bio-information based on the first bio-information. For example, in the case of estimating the bio-information based on the bio-signal, an offset parameter may vary depending on a measurement point of a pulse or a pulse wave signal and individual characteristics of a user. Accordingly, it is required to correct an offset parameter of the estimated bio-information, and the processor 430 may correct the offset parameter of the second bio-information based on the first bio-information.

Based on the measurement time information, the processor 430 may synchronize the first bio-information with the second bio-information, and may estimate the second bio-information by correcting the offset parameter of the second bio-information based on the first bio-information.

For example, if the second bio-information is corrected based on the first bio-information when the first bio-signal and the second bio-signal are not temporally synchronized, accuracy of a correction value may not be guaranteed. For this reason, the processor 430 may correct the offset parameter of the second bio-information by synchronizing the first bio-signal with the second bio-signal based on the measurement time information of the first bio-signal and the second bio-signal, and by calculating a difference between the first bio-information and the second bio-information.

Upon correcting the offset parameter of the second bio-information based on the first bio-information, the processor 430 may estimate the second bio-information based on the corrected offset parameter of the second bio-information.

In the exemplary embodiment, in the case where the first bio-signal and the second bio-signal are measured at different measurement points, the processor 430 may convert the second bio-signal into the form of a bio-signal measured at the first measurement point based on a bio-signal conversion model which is pre-generated by being measured at each measurement point, and may estimate the second bio-information based on the converted second bio-signal. In this manner, even when the first bio-signal and the second bio-signal are measured by the bio-signal measurer 410 at different measurement points, the processor 430 may estimate the second bio-information by converting the bio-signal into a bio-signal and/or bio-information measured at any one measurement point based on a bio-signal conversion model which is pre-generated based on a correlation between bio-signals measured at various measurement points, thereby estimating and correcting the second bio-information more accurately.

In another exemplary embodiment, in the case where the bio-signal measurer 410 includes only one measurement module, such that measurements of the first bio-signal and the second bio-signal are temporally separated, and the first bio-signal and the second bio-signal may not be temporally synchronized, for example, in the case where the first bio-signal is measured during a time period of $t_1$ to $t_2$ and the second bio-signal is measured during a time period of $t_3$ to $t_4$, the processor 430 may not estimate the second bio-information based on the second bio-signal, because no second bio-signal is input while the first bio-signal is measured. As described above, in the case where estimation of the second bio-information and correction of the offset parameter by using the first bio-information may not be performed at the same time, the processor 430 may correct the offset parameter by loading the first bio-information which is pre-stored when estimating the second bio-information, and may estimate the second bio-information. For convenience of explanation, description is made by assuming a case where the first bio-information is measured first and stored, but the exemplary embodiments is not limited to the measurement sequence of the first bio-information and/or the second bio-information.

Further, the processor 430 may synchronize the first bio-information with the second bio-information by determining a measurement time of the first bio-information based on at least one of the measurement time of bio-signals that is recorded by the time recorder, a change in bio-signals, and input of a detection time of the first bio-information, which are measurement time information of the first bio-signal and the second bio-signal.

In the exemplary embodiment, the processor 430 may determine measurement circumstances based on at least one of the types of a bio-signal and/or bio-information, a measurement point, a detection state of a bio-signal, a correction history of the second bio-information, a sampling rate, and motion noise in the detected bio-signal.

Upon determining the measurement circumstances, the processor 430 may determine whether to correct the second bio-information, whether to index the measurement circumstances, and whether to display and store the second bio-information. For example, if the measurement circumstances are determined to be a case where the motion noise (e.g., a signal to ratio (SNR), etc.) in the detected bio-signal exceeds a predetermined threshold, the processor 430 may determine to correct the second bio-information, to index the measurement circumstances at the time of correction to the corrected second bio-signal, or to output or store the second bio-information as a result.

Figure 5:
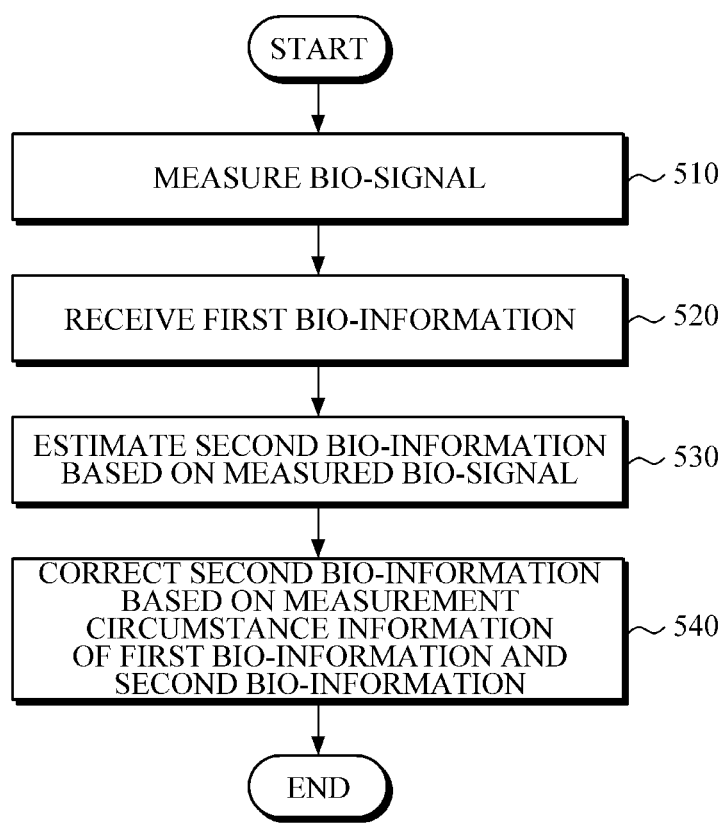
FIG. 5 is a flowchart illustrating a bio-information processing method according to an exemplary embodiment.

FIG. 5 is a flowchart illustrating a bio-information processing method according to an exemplary embodiment. The bio-information processing method of FIG. 5 may be performed by the bio-information processing apparatuses 100 and 200 illustrated in FIGS. 1 and 2.

Referring to FIGS. 1 and 5, the bio-information processing apparatus 100 may measure a bio-signal in operation 510.

The bio-information processing apparatus 100 may measure a bio-signal of a user. For example, the bio-information processing apparatus 100 may include a contact pressure sensor or a pulse wave sensor to measure a bio-signal, and may measure a bio-signal, such as a user's pulse or pulse waves, by measuring a strain gauge using the contact pressure sensor, or by detecting an optical signal using a detector of the pulse wave sensor.

The bio-information processing apparatus 100 may receive the first bio-information in operation 520.

In the exemplary embodiment, the bio-information processing apparatus 100 may receive the first bio-information (e.g., reference bio-information) which is used as a reference for comparison with bio-information estimated from the bio-signal.

For example, the bio-information processing apparatus 100 may receive the first bio-information from an external device by communicating with the external device. Further, the bio-information processing apparatus 100 may receive bio-information by directly connecting to or communicating with the external device, and may also receive the bio-information via one or more relay servers for relaying communication between the bio-information processing apparatus 100 with the external device.

Here, examples of the external device may include a cuff-type blood pressure measuring device, a medical diagnostic device, a cellular phone, a smartphone, a tablet PC, a laptop computer, a personal digital assistant (PDA), a portable multimedia player (PMP), a navigation, an MP3 player, a digital camera, a wearable device, and the like. However, the external device is not limited to the above examples, and may be various devices that may measure or store bio-information of a user.

The bio-information processing apparatus 100 may estimate the second bio-information based on the measured bio-signal in operation 530.

The bio-information processing apparatus 100 may estimate the second bio-information based on the bio-signal measured by the bio-signal measurer 110. For example, the bio-information processing apparatus 100 may estimate the bio-information from the bio-signal by using a bio-information estimation model (e.g., regression model, machine learning model, etc.), which defines a correlation between the measured bio-signal and bio-information.

For example, the bio-information processing apparatus 100 may estimate blood pressure by calculating a pulse transit time (PTT) and a pulse wave velocity (PWV) based on a pulse and/or a pulse wave signal measured by the bio-signal measurer 110, or may estimate blood pressure by using pulse wave analysis (PWA) which analyzes the shape of pulse waves.

The bio-information processing apparatus 100 may synchronize the first bio-information with the second bio-information based on the measurement time information, and may correct the offset parameter of the second bio-information based on the first bio-information.

That is, in the case of measuring the bio-signal, and estimating the second bio-information based on the measured bio-signal, the bio-information processing apparatus 100 may estimate the second bio-information more accurately by correcting the offset parameter of the second bio-information based on the first bio-information.

In this case, the bio-information processing apparatus 100 may synchronize the first bio-information with the second bio-information by determining a measurement time of the first bio-information based on at least one of a time when the first bio-information is received, a change in the bio-signal, and input of a detection time of the first bio-information, and may correct the offset parameter of the second bio-information.

In the case where the bio-information processing apparatus 100 may not know or determine the measurement time of the first bio-information, for example, in the case where the bio-information processing apparatus 100 does not receive the first bio-information according to a user's selection or need, or in the case where the bio-information processing apparatus 100 may not receive bio-information, or there are no feature points to specify a measurement time in the received first bio-information, the bio-information processing apparatus 100 may correct the offset parameter of the second bio-information by applying the measured bio-signal to a pre-generated offset parameter correction model.

Here, the offset parameter correction model may be a correction model pre-generated into one or more groups according to measurement circumstances, which include at least one of the types of a bio-signal and/or bio-information, a measurement point, a detection state of a bio-signal, a correction history of the second bio-information, a sampling rate, and motion noise in the detected bio-signal, and according to user information which includes at least one of age, gender, race, weight, BMI, health information history of a user.

The bio-information processing apparatus 100 may correct the second bio-information based on the measurement circumstances of the first bio-information and the second bio-information in operation 540.

In the exemplary embodiment, the bio-information processing apparatus 100 may determine measurement circumstances based on at least one of the types of a bio-signal and/or bio-information, a measurement point, a detection state of a bio-signal, a correction history of the second bio-information, a sampling rate, and motion noise in the detected bio-signal. The determined measurement circumstances may include circumstances where a bio-signal is measured at the time of measuring a bio-signal, such as a case where measurement points are different and a case where a bloodstream change occurs due to pressure.

Upon determining the measurement circumstances, the bio-information processing apparatus 100 may determine whether to correct the second bio-information, whether to index the measurement circumstances, and whether to display and store the second bio-information. For example, if the measurement circumstances are determined to be a case where the motion noise (e.g., a signal to ratio (SNR), etc.) in the detected bio-signal exceeds a predetermined threshold, the bio-information processing apparatus 100 may determine to correct the second bio-information, to index the measurement circumstances at the time of correction to the corrected second bio-signal, or to output or store the second bio-information as a result.

In this manner, by selectively varying data processing, such as correction of the second bio-information or storage of data, based on the determined measurement circumstances, the bio-information processing apparatus 100 may optimally use a limited operating environment.

Figure 6:
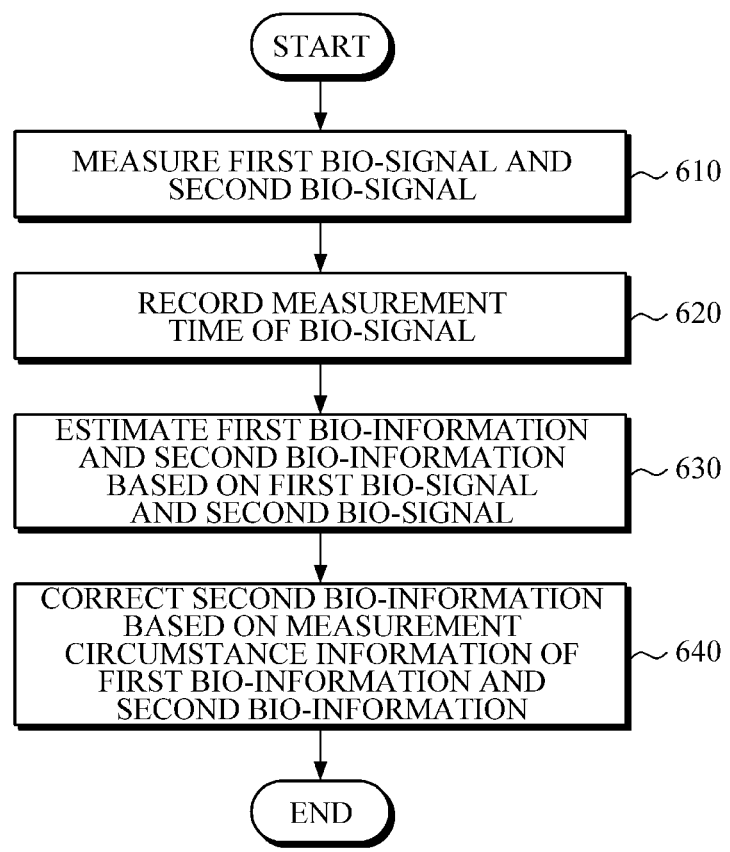
FIG. 6 is a flowchart illustrating a bio-information processing method according to another exemplary embodiment.

FIG. 6 is a flowchart illustrating a bio-information processing method according to another exemplary embodiment. The bio-information processing method of FIG. 6 may be performed by bio-information processing apparatus 400 illustrated in FIG. 4.

The bio-information processing apparatus 400 may measure the first bio-signal and the second bio-signal in operation 610.

In the exemplary embodiment, the bio-information processing apparatus 400 may include one or more measurement modules to measure a bio-signal. In the case where the bio-information processing apparatus 400 includes at least two or more measurement modules, each measurement module may be disposed at different positions. In this case, at least one measurement module may be disposed at a measurement point to measure a reference bio-signal required for correction of bio-information. For example, the bio-information processing apparatus 400 may measure a first bio-signal at a first measurement point (e.g., upper arm, finger, etc.), and a second bio-signal at a second measurement point (e.g., wrist, etc.). In this case, different bio-signal measurement modules are disposed separately at the first measurement point and the second measurement point, such that the first bio-signal and the second bio-signal may be measured at the same time.

The bio-information processing apparatus 400 may record a measurement time of a bio-signal in operation 620.

In the exemplary embodiment, the bio-information processing apparatus 400 may record the measurement time of the bio-signal. For example, the bio-information processing apparatus 400 may record a measurement time and a continuous measurement time of the first bio-signal and the second bio-signal, and may label the measured bio-signal with time information.

For example, in the case where measurement points or measurement times of the first bio-signal and the second bio-signal are different, or in the case where a time difference occurs due to an operation speed difference in a process of estimating bio-information based on the first bio-signal and the second bio-signal, the bio-information processing apparatus 400 may temporally synchronize the first bio-signal with the second bio-signal based on the recorded measurement times of the bio-signals.

The bio-information processing apparatus 400 may estimate the first bio-information and the second bio-information based on the first bio-signal and the second bio-signal in operation 630.

In the exemplary embodiment, the bio-information processing apparatus 400 may estimate the first bio-information and the second bio-information from the first bio-signal and the second bio-signal by using a bio-information estimation model (e.g., regression model, neural network model, etc.) which defines a correlation between the measured bio-signal and the bio-information. For example, the bio-information processing apparatus 400 may estimate blood pressure by calculating a pulse transit time (PTT) and a pulse wave velocity (PWV) based on a measured pulse and/or a pulse wave signal, or may estimate blood pressure by using pulse wave analysis (PWA) which analyzes the shape of pulse waves.

Upon estimating the first bio-information and the second bio-information, the bio-information processing apparatus 400 may correct the second bio-information based on the first bio-information. For example, in the case of estimating the bio-information based on the bio-signal, an offset parameter may vary depending on a measurement point of a pulse and/or a pulse wave signal or individual characteristics of a user. Accordingly, it is required to correct an offset parameter of the estimated bio-information, and the bio-information processing apparatus 400 may correct the offset parameter of the second bio-information based on the first bio-information.

Based on the measurement time information, the bio-information processing apparatus 400 may synchronize the first bio-information with the second bio-information.

For example, if the second bio-information is corrected based on the first bio-information when the first bio-signal and the second bio-signal are not temporally synchronized, accuracy of a correction value may not be guaranteed. For this reason, the bio-information processing apparatus 400 may correct the offset parameter of the second bio-information by synchronizing the first bio-signal with the second bio-signal based on the measurement time information of the first bio-signal and the second bio-signal, and by calculating a difference between the first bio-information and the second bio-information.

The bio-information processing apparatus 400 may correct the second bio-information based on measurement circumstances of the first bio-information and the second bio-information in operation 640.

In the exemplary embodiment, the bio-information processing apparatus 400 may determine measurement circumstances based on at least one of the types of a bio-signal and/or bio-information, a measurement point, a detection state of a bio-signal, a correction history of the second bio-information, a sampling rate, and motion noise in the detected bio-signal.

Upon determining the measurement circumstances, the bio-information processing apparatus 400 may determine whether to correct the second bio-information, whether to index the measurement circumstances, and whether to display and store the second bio-information. For example, if the measurement circumstances are determined to be a case where the motion noise (e.g., a signal to ratio (SNR), etc.) in the detected bio-signal exceeds a predetermined threshold, the bio-information processing apparatus 400 may determine to correct the second bio-information, to index the measurement circumstances at the time of correction to the corrected second bio-signal, or to output or store the second bio-information as a result.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-information processing apparatus comprising:
   a spectrometer configured to measure a bio-signal;
   a communication interface configured to receive first bio-information of a reference bio-signal from an external device;
   a processor configured to estimate second bio-information based on the bio-signal, determine a first measurement time of the first bio-information based on a receipt time of the first bio-information from the external device, and correct the second bio-information based on the first measurement time of the first bio-information and a second measurement time of the second bio-information, wherein the bio-signal is measured by the spectrometer at the second measurement time; and
   a display configured to, in response to a request to correct the second bio-information being received at a first correction request time, display in a time domain a first graph that represents first correction information of the second bio-information, and in response to a request to correct the second bio-information being received at a second correction request time subsequent to the first correction request time, display an identification mark that represents the second correction request time on the first graph, and display in the time domain a second graph that represents second correction information of the second bio-information before and after the second correction request time, so that a portion of the second graph representing the second correction information overlaps with the first graph representing the first correction information from a time between the first correction request time and the second correction request time, to the second correction request time, wherein the processor is further configured to estimate the second bio-information by synchronizing the first bio-information with the second bio-information based on the first measurement time of the first bio-information and the second measurement time of the second bio-information, and by correcting an offset parameter of the second bio-information based on the first bio-information, and wherein the processor is further configured to, during the time between the first correction request time and the second correction request time, generate both the first graph representing the first correction information of the second bio-information and the second graph representing the second correction information of the second bio-information.

2. The apparatus of claim 1, wherein the processor is further configured to correct the second bio-information based on a sampling rate of the bio-signal and a sampling rate of the reference bio-signal.

3. The apparatus of claim 1, wherein the processor is further configured to correct the offset parameter of the second bio-information by applying the measured bio-signal to a pre-generated offset parameter correction model.

4. The apparatus of claim 1, wherein the processor is further configured to correct the second bio-information based on information of a first measurement point of a body part from which the bio-signal is measured, and a second measurement point of a body part from which the reference bio-signal is measured.

5. The apparatus of claim 4, wherein the processor is further configured to determine whether to correct the second bio-information, and whether to display and store the second bio-information.

6. The apparatus of claim 4, wherein in response to the first measurement point of the bio-signal being different from the second measurement point of the reference bio-signal, the processor is further configured to convert the bio-signal based on a bio-signal conversion model which is pre-generated based on a correlation between sample bio-signals, and to estimate the second bio-information based on the converted bio-signal.

7. The apparatus of claim 4, wherein the processor is further configured to determine the second measurement point based on a user's input of the second measurement point and position information detected by a position detection sensor.

8. The apparatus of claim 1, wherein the processor is further configured to continuously estimate the second bio-information based on a result of correcting the second bio-information based on measurement circumstances of the first bio-information and the second bio-information.

9. The apparatus of claim 1, further comprising an output interface configured to output at least one of the measured bio-signal, the first bio-information, the second bio-information, a result of correcting the second bio-information, correction reliability of the second bio-information, warning information, a continuous measurement result, and a trend graph.

10. The apparatus of claim 1, further comprising an output interface further configured to display the measured bio-signal in a first area of a user interface, and display the corrected second bio-information in a second area of the user interface.

11. The apparatus of claim 1, wherein in response to the second bio-information being corrected at a plurality of times, the processor updates the second bio-information based on a correction result at any one time among the plurality of times.

12. A bio-information processing apparatus comprising:
a spectrometer configured to measure a first bio-signal and a second bio-signal;
a time recorder configured to record a first measurement time of the first bio-signal and a second measurement time of the second bio-signal;
a processor configured to estimate first bio-information and second bio-information based on the first bio-signal and the second bio-signal, and to correct the second bio-information based on information of a first measurement point of a body part from which the first bio-signal is measured, and a second measurement point of a body part from which the second bio-signal is measured; and
a display configured to, in response to a request to correct the second bio-information being received at a first correction request time, display in a time domain a first graph that represents first correction information of the second bio-information, and in response to a request to correct the second bio-information being received at a second correction request time subsequent to the first correction request time, display an identification mark that represents the second correction request time on the first graph, and display in the time domain a second graph that represents second correction information of the corrected second bio-information before and after the second correction request time, so that a portion of the second graph representing the second correction information overlaps with the first graph representing the first correction information from a time between the first correction request time and the second correction request time, to the second correction request time, wherein the processor is further configured to estimate the second bio-information by synchronizing the first bio-information with the second bio-information based on the measurement time and the processing time, and by correcting an offset parameter of the second bio-information based on the first bio-information, and wherein the processor is further configured to, during the time between the first correction request time and the second correction request time, generate both the first graph representing the first correction information of the second bio-information and the second graph representing the second correction information of the second bio-information.

13. The apparatus of claim 12, wherein the processor is further configured to correct the second bio-information based on a sampling rate of the first bio-signal and a sample rate of the second bio-signal.

14. The apparatus of claim 12, wherein the spectrometer comprises a first spectrometer disposed at a first surface of the bio-information processing apparatus, and a second spectrometer disposed at a second surface of the bio-information processing apparatus.

15. A bio-information processing method comprising:
measuring a bio-signal;
receiving first bio-information of a reference bio-signal from an external device;

estimating second bio-information based on the bio-signal;

determining a first measurement time of the first bio-information based on a receipt time of the first bio-information from the external device;

correcting the second bio-information based on the first measurement time of the first bio-information and a second measurement time of the second bio-information, wherein the bio-signal is measured by the spectrometer at the second measurement time; and in response to a request to correct the second bio-information being received at a first correction request time, displaying in a time domain a first graph that represents first correction information of the second bio-information, and in response to a request to correct the second bio-information being received at a second correction request time subsequent to the first correction request time, displaying an identification mark that represents the second correction request time on the first graph, and displaying in the time domain a second graph that represents second correction information of the corrected second bio-information before and after the second correction request time, so that a portion of the second graph representing the second correction information overlaps with the first graph representing the first correction information from a time between the first correction request time and the second correction request time, to the second correction request time;

wherein the estimating the second bio-information comprises:
synchronizing the first bio-information with the second bio-information based on the first measurement time of the first bio-information and the second measurement time of the second bio-information; and
correcting an offset parameter of the second bio-information based on the first bio-information, and wherein the correcting the second bio-information comprises:
during the time between the first correction request time and the second correction request time, generating both the first graph representing the first correction information of the second bio-information and the second graph representing the second correction information of the second bio-information.

16. The bio-information processing method of claim 15, wherein the correcting the second bio-information correcting the second bio-information based on a sampling rate of the bio-signal and a sampling rate of the reference bio-signal.

17. The bio-information processing method of claim 15, wherein the correcting the second bio-information comprises determining, based on the first measurement time and the second measurement time, whether to correct the second bio-information, whether to index measurement circumstances of the first bio-information, and whether to display and store the second bio-information.

* * * * *